United States Patent
Locke et al.

(10) Patent No.: US 11,554,206 B2
(45) Date of Patent: Jan. 17, 2023

(54) NEGATIVE PRESSURE WOUND THERAPY DEVICE USING A VACUUM GENERATING PUMP PROVIDING AUDIBLE THERAPY FEEDBACK

(71) Applicant: KCI LICENSING, INC., San Antonio, TX (US)

(72) Inventors: Christopher B. Locke, Bournemouth (GB); Justin Alexander Long, Lago Vista, TX (US)

(73) Assignee: KCI Licensing, Inc., San Antonio, TX (US)

( * ) Notice: Subject to any disclaimer, the term of this patent is extended or adjusted under 35 U.S.C. 154(b) by 304 days.

(21) Appl. No.: 16/965,783

(22) PCT Filed: Jan. 8, 2019

(86) PCT No.: PCT/US2019/012684
§ 371 (c)(1),
(2) Date: Jul. 29, 2020

(87) PCT Pub. No.: WO2019/152140
PCT Pub. Date: Aug. 8, 2019

(65) Prior Publication Data
US 2021/0038775 A1    Feb. 11, 2021

Related U.S. Application Data

(60) Provisional application No. 62/624,980, filed on Feb. 1, 2018.

(51) Int. Cl.
*A61M 1/00* (2006.01)
*F04B 43/04* (2006.01)

(52) U.S. Cl.
CPC .............. *A61M 1/90* (2021.05); *A61M 1/962* (2021.05); *A61M 1/964* (2021.05); *F04B 43/04* (2013.01);
(Continued)

(58) Field of Classification Search
CPC .. A61M 1/74; A61M 2205/3344; A61M 1/73; A61M 2205/15; A61M 2205/186;
(Continued)

(56) References Cited

U.S. PATENT DOCUMENTS 1,355,846 A    10/1920   Rannells
2,547,758 A     4/1951   Keeling
(Continued)

FOREIGN PATENT DOCUMENTS

AU    550575 B2    3/1986
AU    745271 B2    3/2002
(Continued)

OTHER PUBLICATIONS

He, Lipeng et al. "Exploration on Relationship Between Flow Rate and Sound Pressure Level of Piezoelectric Pump." Microsystem technologies: sensors, actuators, systems integration 26.2 (2019): 609-616. Web.*

(Continued)

*Primary Examiner* — Nicholas J. Weiss
*Assistant Examiner* — Seth Han

(57) ABSTRACT

A negative pressure wound therapy device includes a piezoelectric pump, a state detector configured to detect a state of the pump, and a control circuit configured to transmit a first control signal for a first period having a first RMS voltage greater than or equal to a threshold voltage at which driving the pump for a second period greater than the first period can cause the pump to emit sound at a magnitude greater than a sound threshold; receive a first indication of the state; determine if the pump is in a leak condition; transmit, responsive to the pump not being in the leak condition, a second control signal having a second RMS voltage less than the first RMS voltage; and transmit, responsive to the pump being in the leak condition, a third control signal (Continued)

having a third RMS voltage greater than the second RMS voltage.

20 Claims, 4 Drawing Sheets

(52) U.S. Cl.
CPC ... *A61M 2205/15* (2013.01); *A61M 2205/186* (2013.01); *A61M 2205/3334* (2013.01); *A61M 2205/581* (2013.01); *A61M 2205/583* (2013.01)

(58) Field of Classification Search
CPC ..... A61M 2205/3334; A61M 2205/583; F04B 43/0081; F04B 17/003; F04B 2201/0801; F04B 2201/0806; F04B 2203/0405; F04B 2203/00; F04B 2201/00; F04B 43/046; F04B 49/06
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,123,502 B2 | 2/2012 | Blakey et al. |
| 8,371,829 B2 | 2/2013 | Jaeb et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2008/0200857 A1* | 8/2008 | Lawhorn ............... A61M 1/74 602/41 |
| 2011/0054810 A1* | 3/2011 | Turner ............... A61M 1/74 702/47 |
| 2017/0368239 A1* | 12/2017 | Askem ............... A61M 1/73 |
| 2020/0276367 A1* | 9/2020 | Seddon ............... A61M 1/90 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2 632 406 A1 | 9/2013 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |

(56) References Cited

FOREIGN PATENT DOCUMENTS

| | | |
|---|---|---|
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2012/057881 A1 | 5/2012 |
| WO | WO-2013/171585 A2 | 11/2013 |
| WO | WO-2021/059192 A1 | 4/2021 |

OTHER PUBLICATIONS

International Search Report and Written Opinion on International Patent Application No. PCT/US2019/012684 dated Apr. 10, 2019 (13 pages).

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

NEGATIVE PRESSURE WOUND THERAPY DEVICE USING A VACUUM GENERATING PUMP PROVIDING AUDIBLE THERAPY FEEDBACK

CROSS-REFERENCE TO RELATED APPLICATIONS

This application claims the benefit of priority under 35 U.S.C. § 371 to International Application No. PCT/US2019/012684, filed on Jan. 8, 2019, which claims the benefit of priority to U.S. Provisional Application No. 62/624,980, filed on Feb. 1, 2018, which are incorporated herein by reference in their entirety.

BACKGROUND

The present disclosure relates generally to wound therapy systems and devices, and more particularly to a negative pressure wound therapy device.

Negative pressure wound therapy (NPWT) is a type of wound therapy that involves applying negative pressure (relative to atmosphere pressure) to a wound site to promote wound healing. Some NPWT systems include a pump which operates to maintain the wound site at negative pressure by removing wound exudate from the wound site.

In some existing NPWT systems, a piezoelectric pump is used to apply the negative pressure to the wound site. Piezoelectric pumps can operate at very low noise levels (e.g., silently), which can reduce power requirements while also improving the perceived experience for a user. However, existing NPWT piezoelectric pumps are difficult to maintain in silent operation, due to thermal loading and other inefficiencies that development over the course of use. In addition, in many existing NPWT systems, it is difficult to provide audible indications that the NPWT systems are leaking, particularly due to the desire for silent operation.

SUMMARY

One implementation of the present disclosure is a negative pressure wound therapy (NPWT) device. The NPWT device includes at least one piezoelectric pump, a state detector, and a control circuit. The at least one piezoelectric pump is configured to apply a vacuum to a wound site. The state detector is configured to detect a state of the at least one piezoelectric pump. The control circuit is configured to transmit a first control signal to the at least one piezoelectric pump to drive the at least one piezoelectric pump for a first period of time, the first control signal having a first root mean square (RMS) voltage, the first RMS voltage greater than or equal to a threshold voltage at which driving the at least one piezoelectric pump for at least a second period of time greater than the first period of time causes the at least one piezoelectric pump to emit sound at a magnitude greater than a sound threshold; receive a first indication of the state from the state detector; determine, based on the first indication of the state, if the at least one piezoelectric pump is in a leak condition; transmit, responsive to the at least one piezoelectric pump not being in the leak condition, a second control signal to the at least one piezoelectric pump to drive the at least one piezoelectric pump, the second control signal having a second RMS voltage less than the first RMS voltage; and transmit, responsive to the at least one piezoelectric pump being in the leak condition, a third control signal to the at least one piezoelectric pump to drive the at least one piezoelectric pump, the third control signal having a third RMS voltage greater than the second RMS voltage.

In some embodiments, the control circuit is configured to execute the determination of whether the at least one piezoelectric pump is in the leak condition responsive to expiration of the first period of time.

In some embodiments, the NPWT device includes a display coupled to the control circuit, wherein the control circuit is configured to cause the display to output a visual indication of the leak condition responsive to determining that the at least one piezoelectric pump is in the leak condition and subsequent to the first period of time.

In some embodiments, the control circuit is further configured to receive, subsequent to transmitting the second control signal, a second indication of the state from the state detector; determine, based on the second indication of the state, if the at least one piezoelectric pump is in the leak condition; transmit, responsive to the at least one piezoelectric pump not being in the leak condition, a fourth control signal to the at least one piezoelectric pump to drive the at least one piezoelectric pump, the fourth control signal having a fourth RMS voltage less than the second RMS voltage; and transmit, responsive to the at least one piezoelectric pump being in the leak condition, a fifth control signal to the at least one piezoelectric pump to drive the at least one piezoelectric pump, the fifth control signal having a fifth RMS voltage greater than the second RMS voltage.

In some embodiments, the NPWT device includes a housing at least partially surrounding the at least one piezoelectric pump, the housing configured to increase a loudness outside of the housing of the sound emitted by the at least one piezoelectric pump.

In some embodiments, the housing is shaped to facilitate gas venting from the at least one piezoelectric pump.

In some embodiments, the first RMS voltage is an average RMS voltage, and transmitting the first control signal includes generating the first control signal by modulating at least one of a duty cycle or a magnitude of the first control signal.

In some embodiments, the control circuit is further configured to receive an indication of a user modification of a dressing adjacent to the wound site, and transmit a fourth control signal having a fourth RMS voltage less than the second RMS voltage to the at least one piezoelectric pump responsive to receiving the indication.

In some embodiments, the state detector includes at least one of (i) a flow rate sensor coupled to the at least one piezoelectric pump, the flow rate sensor configured to detect a flow rate through the at least one piezoelectric pump, wherein the control circuit is configured to compare the detected flow rate to a flow rate threshold, and determine the at least one piezoelectric pump to be operating in the leak condition responsive to the flow rate exceeding the flow rate threshold; or (ii) a pressure sensor configured to detect a pressure of at least one of the at least one piezoelectric pump or the wound site, wherein the control circuit is configured to compare the pressure detected by the pressure sensor to a target pressure threshold, and determine the at least one piezoelectric pump to be operating in the leak condition responsive to the pressure being less than the target pressure threshold.

In some embodiments, the sound threshold is zero dB(A).

Another implementation of the present disclosure is a method. The method includes transmitting a first control signal to at least one piezoelectric pump to drive the at least one piezoelectric pump for a first period of time, the at least one piezoelectric pump configured to apply a vacuum to a wound site, the first control signal having a first root mean square (RMS) voltage, the first RMS voltage greater than or equal to a threshold voltage at which driving the at least one piezoelectric pump for at least a second period of time greater than the first period of time causes the at least one piezoelectric pump to emit sound at a magnitude greater than a sound threshold. The method includes receiving, from a state detector configured to detect a state of the at least one piezoelectric pump, a first indication of the state. The method includes determining, based on the first indication of the state, if the at least one piezoelectric pump is in a leak condition. The method includes transmitting, responsive to the at least one piezoelectric pump not being in the leak condition, a second control signal to the at least one piezoelectric pump to drive the at least one piezoelectric pump for a third period of time, the second control signal having a second RMS voltage less than the first RMS voltage. The method includes transmitting, responsive to the at least one piezoelectric pump being in the leak condition, a third control signal to the at least one piezoelectric pump to drive the at least one piezoelectric pump, the third control signal having a third RMS voltage greater than the second RMS voltage.

In some embodiments, determining whether the at least one piezoelectric pump is in the leak condition includes determining whether the at least one piezoelectric pump is in the leak condition responsive to expiration of the first period of time.

In some embodiments, the method includes causing a display to output a visual indication of the leak condition responsive determining that the at least one piezoelectric pump is in the leak condition and subsequent to the first period of time.

In some embodiments, the method includes receiving, responsive to the third period of time expiring, a second indication of the state from the state detector; determining, based on the second indication of the state, if the at least one piezoelectric pump is in the leak condition; transmitting, responsive to the at least one piezoelectric pump not being in the leak condition, a fourth control signal to the at least one piezoelectric pump to drive the at least one piezoelectric pump, the fourth control signal having a fourth RMS voltage less than the second RMS voltage; and transmitting, responsive to the at least one piezoelectric pump being in the leak condition, a fifth control signal to the at least one piezoelectric pump to drive the at least one piezoelectric pump, the fifth control signal having a fifth RMS voltage greater than the second RMS voltage.

In some embodiments, the method includes providing a housing to at least partially surround the at least one piezoelectric pump, the housing configured to increase a loudness outside of the housing of the sound emitted by the at least one piezoelectric pump.

In some embodiments, the housing is shaped to facilitate gas venting from the at least one piezoelectric pump.

In some embodiments, the first RMS voltage is an average RMS voltage, and transmitting the first control signal includes generating the first control signal by modulating at least one of a duty cycle or a magnitude of the first control signal.

In some embodiments, the method includes receiving an indication of a user modification of a dressing adjacent to the wound site, and transmitting a fourth control signal having a fourth RMS voltage less than the second RMS voltage to the at least one piezoelectric pump responsive to receiving the indication.

In some embodiments, the state detector includes at least one of (i) a flow rate coupled to the at least one piezoelectric pump, the leak detector configured to detect a flow rate through the at least one piezoelectric pump, wherein determining the at least one piezoelectric pump to be operating in the leak condition includes determining the flow rate to exceed a flow rate threshold; or (ii) a pressure sensor configured to detect a pressure of at least one of the at least one piezoelectric pump or the wound site, wherein determining the at least one piezoelectric pump to be operating in the leak condition includes determining the pressure to be less than a target pressure threshold.

In some embodiments, the sound threshold is zero dB(A).

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Referring generally to the FIGURES, a negative pressure wound therapy (NPWT) device and components thereof are shown, according to various exemplary embodiments. The NPWT device may include at least one piezoelectric pump, a state detector, and a control circuit. The at least one piezoelectric pump is configured to apply a vacuum to a wound site. The state detector is configured to detect a state of the at least one piezoelectric pump. The control circuit is configured to transmit a first control signal to the at least one piezoelectric pump to drive the at least one piezoelectric pump for a first period of time, the first control signal having a first root mean square (RMS) voltage, the first RMS voltage greater than or equal to a threshold voltage at which driving the at least one piezoelectric pump for at least a second period of time greater than the first period of time causes the at least one piezoelectric pump to emit sound at a magnitude greater than a sound threshold; receive a first indication of the state from the state detector; determine, based on the first indication of the state, if the at least one piezoelectric pump is in a leak condition; transmit, responsive to the at least one piezoelectric pump not being in the leak condition, a second control signal to the at least one piezoelectric pump to drive the at least one piezoelectric pump, the second control signal having a second RMS voltage less than the first RMS voltage; and transmit, responsive to the at least one piezoelectric pump being in the leak condition, a third control signal to the at least one piezoelectric pump to drive the at least one piezoelectric pump, the third control signal having a third RMS voltage greater than the second RMS voltage.

In some embodiments, the NPWT system of the present solution improves on existing systems by taking advantage of the unexpected feature of the at least one piezoelectric pump that the at least one piezoelectric pump, though typically operated in a silent mode, can be driven at certain voltages for certain amounts of time which can cause the at least one piezoelectric pump to emit an audible sound (e.g., at a loudness greater than a noise threshold for silent operation). As such, the solutions described herein can use the at least one piezoelectric pump to act as a sounder component, without requiring dedicated audio output electronics which would otherwise increase the size, cost, weight, power usage, and/or heat generation by the NPWT system.

Negative Pressure Wound Therapy System

Figure 1:
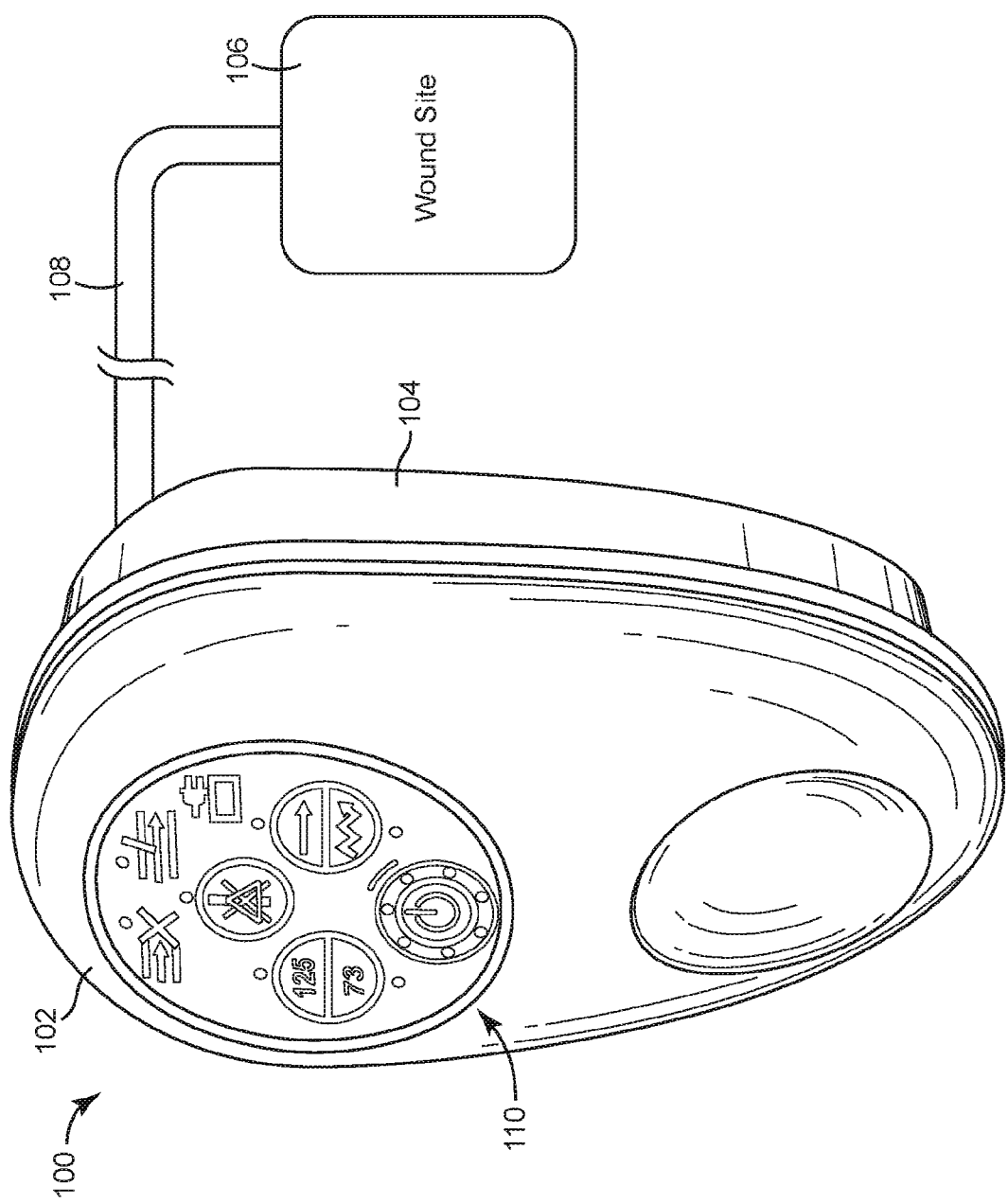
FIG. 1 is a drawing of a negative pressure wound therapy (NPWT) system including a NPWT device fluidly connected with a wound site, according to an exemplary embodiment.
Figure 2:
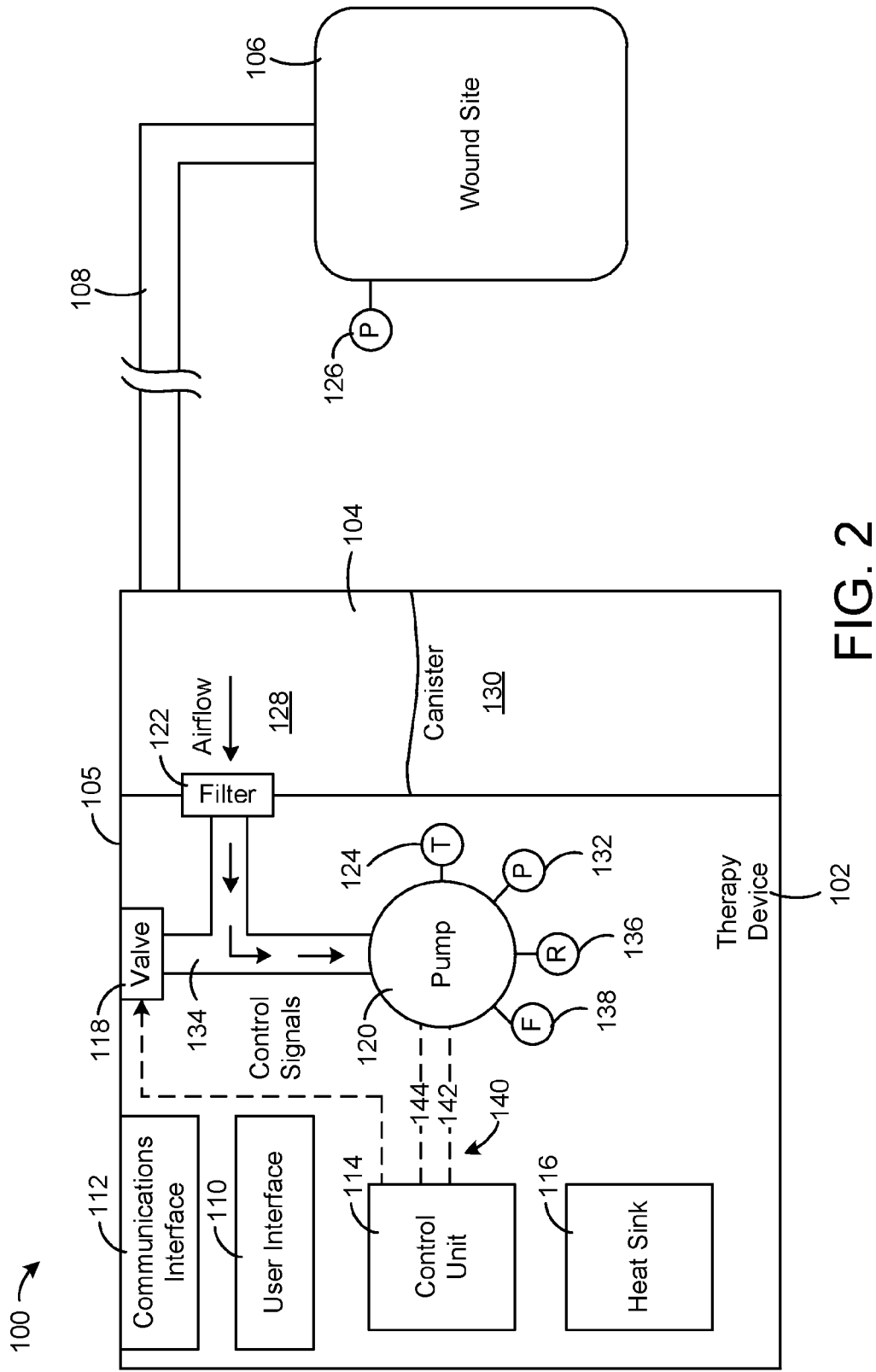
FIG. 2 is a block diagram illustrating the NPWT device of FIG. 1 in greater detail, according to an exemplary embodiment.

Referring now to FIGS. 1-2, a negative pressure wound therapy (NPWT) system 100 is shown, according to an exemplary embodiment. NPWT system 100 is shown to include a therapy device 102 fluidly connected to a wound site 106 via tubing 108. Wound site 106 may include a tissue wound as well as a wound dressing that covers the tissue wound and adheres to a patient's skin. Several examples of wound dressings which can be used in combination with NPWT system 100 are described in detail in U.S. Pat. No. 7,651,484 granted Jan. 26, 2010, U.S. Pat. No. 8,394,081 granted Mar. 12, 2013, and U.S. patent application Ser. No. 14/087,418 filed Nov. 22, 2013. The entire disclosure of each of these patents and patent applications is incorporated by reference herein.

Therapy device 102 can be configured to provide negative pressure wound therapy by reducing the pressure at wound site 106. Therapy device 102 can draw a vacuum at wound site 106 (relative to atmospheric pressure) by removing wound exudate, air, and other fluids from wound site 106. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound site 106 may include instillation fluid previously delivered to wound site 106. Instillation fluid can include, for example, a cleansing fluid, a prescribed fluid, a medicated fluid, an antibiotic fluid, or any other type of fluid which can be delivered to wound site 106 during wound treatment.

The fluids removed from wound site 106 pass through tubing 108 and are collected in canister 104, in some embodiments. Canister 104 may be a component of therapy device 102 configured to collect wound exudate and other fluids removed from wound site 106. In some embodiments, canister 104 is detachable from therapy device 102 to allow canister 104 to be emptied and replaced as needed. A lower portion 130 of canister 104 may be filled with wound exudate and other fluids removed from wound site 106, whereas an upper portion 128 of canister 104 may be filled with air. Therapy device 102 can be configured to draw a vacuum within canister 104 by pumping air out of canister 104. The reduced pressure within canister 104 can be translated to wound site 106 via tubing 108 such that wound site 106 is maintained at the same pressure as canister 104.

Referring particularly to FIG. 2, a block diagram illustrating therapy device 102 in greater detail is shown, according to an exemplary embodiment. Therapy device 102 is shown to include a housing 105, a pump 120, a filter 122, a valve 118, a heat sink 116, and a control unit 114. Pump 120 can be fluidly coupled to canister 104 (e.g., via conduit 134) and can be configured to draw a vacuum within canister 104 by pumping air out of canister 104. In some embodiments, pump 120 is configured to operate in both a forward direction and a reverse direction. For example, pump 120 can operate in the forward direction to pump air out of canister 104 and decrease the pressure within canister 104. Pump 120 can operate in the reverse direction to pump air into canister 104 and increase the pressure within canister 104. Pump 120 can be controlled by control unit 114, described in greater detail below.

Housing 105 at least partially surrounds components of therapy device 102, such as pump 120. Housing 105 can increase a loudness of sound emitted by pump 120 as perceived outside of housing 105. The loudness may be increased relative to a baseline loudness (e.g., of existing enclosures, which may be designed to reduce the loudness of sound emitted by pump 120 as part of silent operation of pump 120). For example, housing 105 can include one or more baffles or other features known to those skilled in the art which increase the loudness of the sound emitted by pump 120. In some embodiments, housing 105 increases or optimizes a rate of gas venting from pump 120, such as when pump 120 is operating to apply a vacuum to wound site 106.

Pump 120 is a piezoelectric pump. In some embodiments, the pump 120 includes a movable member (e.g., diaphragm) which undergoes mechanical displacement based on a voltage applied to the movable member, such as by oscillating in response to receiving an alternating current. By oscillating, the movable member can push air to generate the negative pressure applied by the pump 120. The movable member can be metallic. Pump 120 can include a copper disc with a slit which opens when pushed by the movable member. In some embodiments, the movable member oscillates at approximately 21 kHz. Under typical operational conditions, the pump 120 can operate silently or near silently. For example, noise generated by pump 120 can be less than a noise threshold which can be heard by a typical user. In some embodiments, the noise threshold is less than 30 dB(A). In some embodiments, the noise threshold is less than or equal to 10 dB(A). In some embodiments, the noise threshold is 0 db(A). In an embodiment, pump 120 is a Vacuum Pump manufactured by Koge Micro Tech Co., Ltd.

In some embodiments, NPWT system 100 includes a plurality of pumps 120. For example, therapy device 102 may include multiple pumps 120, each coupled to tubing 108 and controlled by control unit 114. NPWT system 100 may include a plurality of therapy devices 102, each of which may include one or more pumps 120.

Filter 122 can be positioned between canister 104 and pump 120 (e.g., along conduit 134) such that the air pumped out of canister 104 passes through filter 122. Filter 122 can be configured to prevent liquid or solid particles from entering conduit 134 and reaching pump 120. Filter 122 may include, for example, a bacterial filter that is hydrophobic and/or lipophilic such that aqueous and/or oily liquids will bead on the surface of filter 122. Pump 120 can be configured to provide sufficient airflow through filter 122 that the pressure drop across filter 122 is not substantial (e.g., such that the pressure drop will not substantially interfere with the application of negative pressure to wound site 106 from therapy device 102).

Figure 3:
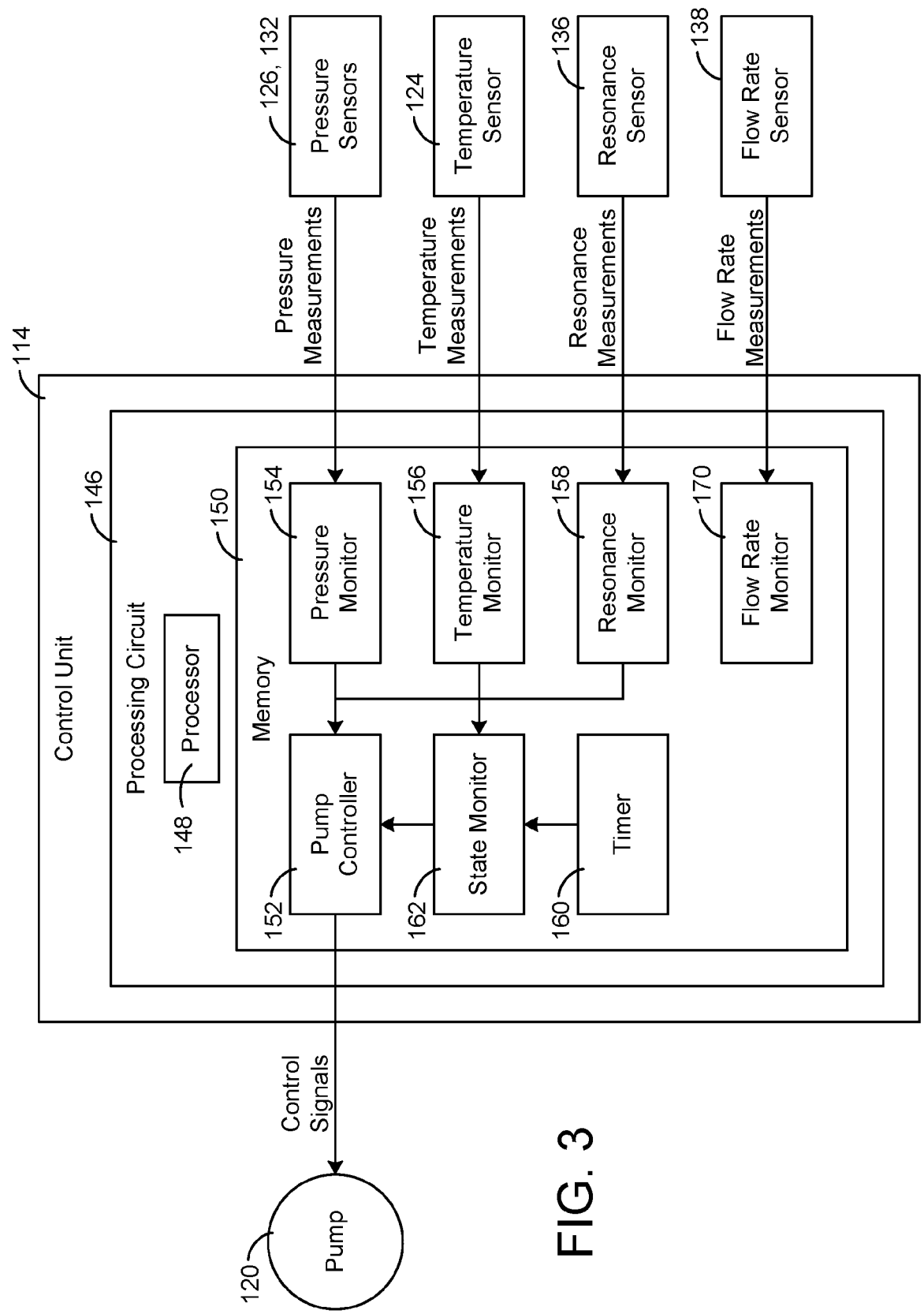
FIG. 3 is a block diagram of a control unit of the NPWT device of FIG. 1, according to an exemplary embodiment.

Valve 118 can be fluidly connected with pump 120 and filter 122 via conduit 134. In some embodiments, valve 118 is configured to control airflow between conduit 134 and the environment around therapy device 102. For example, valve 118 can be opened to allow airflow between conduit 134 and the environment around therapy device 102, and closed to prevent airflow between conduit 134 and the environment around therapy device 102. Valve 118 can be opened and closed by control unit 114, described in greater detail below. When valve 118 is closed, pump 120 can draw a vacuum within conduit 134 and canister 104 by causing airflow through filter 122 in a first direction, as shown in FIG. 2. When valve 118 is open, airflow from the environment around therapy device 102 may enter conduit 134 and fill the vacuum within conduit 134 and canister 104. The airflow from conduit 134 into canister 104 may pass through filter 122 in a second direction, opposite the first direction, as shown in FIG. 3.

While FIG. 2 illustrates the use of the canister 104 and filter 122, it will be appreciated that in some embodiments, the therapy device 102 may not include either the canister 104 or the filter 122, such that the pump 120 may be directly coupled to the wound site 106 via the tubing 108.

Heat sink 116 may be provided to increase a rate of heat dissipation from therapy device 102 or components thereof, such as pump 120. For example, heat sink 116 can be configured to have a relatively greater coefficient for convective heat transfer than other components of therapy device 102, such as by having a relatively greater surface area to volume ratio. Heat sink 116 may be mounted to control unit 114, pump 120, or a circuit board (not shown) to which control unit 114 and/or pump 120 are mounted. In some embodiments, heat sink 116 includes a plurality of fins.

Control unit 114 can be configured to operate pump 120, valve 118, and/or other controllable components of therapy device 102. In some embodiments, control unit 114 is configured to operate pump 120 by transmitting a control signal to pump 120 via alternating current circuit 140, which includes first arm 142 and second arm 144. The arms 142, 144 may be associated with corresponding pump drive electrodes for pump 120.

In some embodiments, therapy device 102 includes a variety of state detectors (e.g., sensors), which can communicate sensor measurements to control unit 114. For example, therapy device 102 is shown to include a temperature sensor 124 configured to measure a temperature of pump 120 and communicate the measured temperature of pump 120 to control unit 114. Temperature sensor 124 may be a thermocouple.

In some embodiments, NPWT system 100 includes a pressure sensor 126 configured to measure the pressure at wound site 106 and communicate the measured pressure to control unit 114. NPWT system 100 may also include a pressure sensor 132 configured to measure the pressure at the pump, and a resonance sensor 136 configured to measure a resonance of pump 120 (e.g., of the movable member of pump 120). Control unit 114 can use the sensor measurements as inputs to various control operations performed by control unit 114 (described in greater detail with reference to FIG. 4).

NPWT system 100 may include a flow rate sensor 138 configured to detect a flow rate through pump 120 (e.g., a flow rate as applied by pump 120 to wound site 106). The flow rate sensor 138 may be coupled to pump 120, or to other points on a flow path from wound site 106 to pump 120 in order to detect the flow rate through pump 120.

In some embodiments, therapy device 102 includes a user interface 110. User interface 110 may include one or more buttons, dials, sliders, keys, or other input devices configured to receive input from a user. User interface 110 may also include one or more display devices (e.g., LEDs, LCD displays, etc.), speakers, tactile feedback devices, or other output devices configured to provide information to a user. In some embodiments, the pressure measurements recorded by pressure sensors 124-126 and the orientation measurements recorded by orientation sensor 132 are presented to a user via user interface 110. User interface 110 can also display alerts generated by control unit 114.

In some embodiments, therapy device 102 includes a data communications interface 112 (e.g., a USB port, a wireless transceiver, etc.) configured to receive and transmit data. Communications interface 112 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 112 can include a USB port or an Ethernet card and port for sending and receiving data via an Ethernet-based communications link or network. In another example, communications interface 112 can include a Wi-Fi transceiver for communicating via a wireless communications network or cellular or mobile phone communications transceivers.

Control Unit

Referring now to FIG. 3, a block diagram illustrating control unit 114 in greater detail is shown, according to an exemplary embodiment. Control unit 114 is shown to include a processing circuit 146 including a processor 148 and memory 150. Processor 148 may be a general purpose or specific purpose processor, an application specific integrated circuit (ASIC), one or more field programmable gate arrays (FPGAs), a group of processing components, or other suitable processing components. Processor 148 is configured to execute computer code or instructions stored in memory 150 or received from other computer readable media (e.g., CDROM, network storage, a remote server, etc.).

Memory 150 may include one or more devices (e.g., memory units, memory devices, storage devices, etc.) for storing data and/or computer code for completing and/or facilitating the various processes described in the present disclosure. Memory 150 may include random access memory (RAM), read-only memory (ROM), hard drive storage, temporary storage, non-volatile memory, flash memory, optical memory, or any other suitable memory for storing software objects and/or computer instructions. Memory 150 may include database components, object code components, script components, or any other type of information structure for supporting the various activities and information structures described in the present disclosure. Memory 150 may be communicably connected to processor 148 via processing circuit 146 and may include computer code for executing (e.g., by processor 148) one or more processes described herein. When processor 148 executes instructions stored in memory 150, processor 148 generally configures control unit 114 (and more particularly processing circuit 146) to complete such activities.

Control unit 114 is shown to include a pump controller 152. Pump controller 152 generates control signals to control operation of pump 120. Pump controller 152 can configure parameters of the control signals, such as current, voltage, frequency, amplitude, or intermittency. In some embodiments, pump controller 152 generates alternating current control signals having a root mean square (RMS) voltage, and transmits the control signals to pump 120 via alternating current circuit 140 (as shown in FIG. 3). For example, pump controller 152 can generate the control signals to have a particular RMS voltage by modulating a first phase angle of a first signal component associated with first arm 142 relative to a second phase angle of a second signal component associated with second arm 144. The RMS voltage can be an average RMS voltage, and control unit 114 can modulate the RMS voltage by at least one of modulating a duty cycle or a magnitude of the control signal.

Pump controller 152 can modulate the control signals to have specified waveforms. For example, pump controller 152 can modulate the control signals to have square, triangular, or sinusoidal waveforms. Square waveforms may result in thermal loading of pump 120 by oscillating between peak voltages of opposite signs, spending more time at peak voltage such that the transition between the peaks opposite signs is abrupt. Triangular waveforms may have reduced effectiveness by having amplitudes near the peaks for a relatively low fraction of the total waveform duration. In some embodiments, pump controller 152 can improve operation of pump 120 by modulating the control signals to have sinusoidal waveforms (see FIG. 5B), which provides smooth transitions between peaks and valleys, efficiently applying the alternating current signal to pump 120 while reducing the likelihood of undesired thermal loading. For example, it will be appreciated that the sinusoidal waveform can be smooth, as compared to the square waveform, which can include a step function transition from a minimum value to a maximum value (see FIG. 5A); or a triangular waveform, which can include a sharp corner where a slope of the waveform changes sign instantaneously or near instantaneously. In some embodiments, the sinusoidal waveform is based on a single sine (or cosine) wave function (as compared to a square waveform or triangular waveform, which may be generated by combining multiple sine wave functions of varying amplitudes). Pump controller 152 can modulate the sinusoidal control signals to have particular RMS voltages by modulating the first phase angle of the first sinusoidal signal component associated with first arm 142 relative to the second phase angle of the second sinusoidal signal component associated with second arm 144.

In some embodiments, pump controller 152 modulates voltage of the control signal by modulating a first phase angle of a first signal component associated with first arm 142 relative to a second phase angle of a second signal component associated with second arm 144. For example, pump controller 152 can initially output the control signal with the first phase angle being 180 degrees offset from the second phase angle, and increase the voltage by reducing the offset (e.g., reducing from 180 degrees towards 0 degrees). As such, pump controller 152 can more quickly achieve a desired voltage than by existing methods based on calculating voltage. In addition, pump controller 152 can reduce computational burden by changing the phase angle, which can avoid either (1) requiring multiply/divide capability or (2) re-programming memory each time amplitude is changed.

Control unit 114 is shown to include a pressure monitor 154. Pressure monitor 154 can be configured to monitor the pressure within pump 120 and/or the pressure at wound site 106 using feedback from pressure sensors 124-126. For example, pressure sensors 124-126 may provide pressure measurements to pressure monitor 154. Pressure monitor 154 can use the pressure measurements to determine the pressure within pump 120 and/or the pressure at wound site 106 in real-time. Pressure monitor 154 can provide the pressure value to state monitor 162 and/or pump controller 152 for use as an input to control processes performed by such components.

Control unit 114 can include a temperature monitor 156. Temperature monitor 156 can monitor the temperature of pump 120 using temperature measurements from temperature sensor 124, and use the temperature measurements to calculate the temperature of pump 120, in real-time. Similar to pressure monitor 154, temperature monitor 156 can provide the temperature of pump 120 to state monitor 162 and/or pump controller 152 for use as an input to control processes performed by such components.

In some embodiments, control unit 114 includes a resonance monitor 158. Resonance monitor 158 can receive resonance measurements from resonance sensor 136, and determine a resonance frequency of pump 120, in real-time. Similar to pressure monitor 154 and temperature monitor 156, resonance monitor 158 can transmit the determined resonance frequency to state monitor 162 and/or pump controller 152 for use as an input to control processes performed by such components.

In some embodiments, control unit 114 includes a flow rate monitor 170 configured to monitor flow rates through pump 120. Flow rate monitor 170 can receive flow rate measurements from flow rate sensor 138 and calculate the flow rate through pump 120 based on the flow rate measurements. Flow rate monitor 170 can provide the flow rate to state monitor 162 and/or pump controller 152 for use as an input to control processes performed by such components.

Control unit 114 includes a timer 160, in some embodiments. Control unit 114 (or components thereof, such as pump controller 152) can initiate and/or reset timer 160 in response to various trigger conditions. For example, control unit 114 can initiate timer 160 responsive to pump controller 152 transmitting a control signal (e.g., a control signal having a first RMS voltage) to pump 120. Control unit 114 can reset timer 160 responsive to transmitting a control signal (e.g., a control signal having a second RMS voltage) to pump 120. Control unit 114 can use timer 160 to determine when to poll sensor values from monitors 154, 156, 158, 170. Timer 160 can store various periods of time associated with specific control signals. Timer 160 can output a time to state monitor 162 and/or pump controller 152 for use as an input to control processes performed by such components.

In some embodiments, control unit 114 includes a state monitor 162. State monitor 162 can receive sensor measurements from sensors 124, 126, 132, 136, 138 (e.g., via corresponding monitors 154, 156, 158, 170), and execute operations using the received sensor measurements. State monitor 162 can also receive the time outputted by timer 160. In various embodiments, state monitor 162 is configured to determine whether a state of pump 120 indicates that pump 120 is overheating or may be susceptible to overheating, which can allow pump controller 152 to modify control of pump 120 before noise generation, overheating, or other undesired conditions of pump 120 occur.

State monitor 162 can determine if pump 120 is in a leak condition based on state information received from sensors 124, 126, 132, 136, 138 via corresponding monitors 154, 156, 158, 170. The leak condition may be indicative of pump 120 failing to complete a draw-down of the wound dressing which covers wound site 106, and thus potentially faulty operation of NPWT system 100. The leak condition may be consistent with the flow rate through pump 120 being greater than an expected flow rate for a given RMS voltage at which pump 120 is driven.

State monitor 162 can determine pump 120 to be in the leak condition based on a flow rate received from flow rate monitor 170. For example, state monitor 162 can compare the flow rate to a flow rate threshold, and determine pump 120 to be operating in the leak condition responsive to the flow rate exceeding the flow rate threshold. It will be appreciated that the flow rate threshold may depend on design characteristics of NPWT system 100. In some embodiments, the flow rate threshold is 80 cc/min.

State monitor 162 can determine pump 120 to be in the leak condition based on a pressure received from pressure monitor 154. For example, state monitor 162 can compare the pressure to a target pressure threshold, and determine pump 120 to be operating in the leak condition responsive to the pressure being less than the target pressure threshold. It will be appreciated that the pressure threshold may depend on design characteristics of NPWT system 100. In some embodiments, the target pressure threshold is 125 mmHg. In some embodiments, state monitor 162 determines pump 120 to be operating in the leak condition based on the pressure being less than the pressure threshold subsequent to an initial draw down period of time, during which pump 120 may be driven at a relatively high RMS voltage. As such, the leak condition can be determined when pump 120 fails to achieve the target pressure threshold after the initial draw down period of time. Similarly, state monitor 162 can periodically monitor the pressure by comparing the pressure to the target pressure threshold (even after the target pressure has been achieved) to determine if pump 120 is operating in the leak condition at various points in time.

State monitor 162 can receive an indication of a user modification of the dressing adjacent to wound site 106. For example, state monitor 162 can receive an indication that a user is attempting to adjust the dressing to address a leak. The indication may be received from a position sensor (not shown) coupled to or adjacent to the dressing. State monitor 162 can also detect the indication based on a rate of change of a state variable such as at least one of the flow rate through pump 120 or the pressure of pump 120 or wound site 106. For example, state monitor 162 can calculate the rate of change of the state variable, compare the rate of change to a corresponding threshold rate of change, and detect the indication responsive to the rate of change exceeding the threshold rate of change. In response to receiving the indication of the user modification, state monitor 162 can transmit the indication to pump controller 152 so that pump controller 152 transmits a control signal having a relatively low RMS voltage (e.g., lower than a nominal RMS voltage used when draw down has been achieved). Subsequently, state monitor 162 can monitor the state variable to determine if pump 120 has returned to normal operation, and cause pump controller 152 to transmit a control signal having the nominal RMS voltage used when draw down has been achieved.

State monitor 162 can identify the expiration of various periods of time used to determine which control signals to transmit to pump 120 based on receiving the time from the timer 160. For example, state monitor 162 can periodically receive the time from the timer 160, compare the time to a period of time, and identify the expiration of the period of time based on the time exceeding the period of time. It will be appreciated that the periods of time may vary based on various factors affecting the rate of heat generation, storage, and dissipation by pump 120, such as the composition, size, and/or drive voltage of pump 120.

In some embodiments, state monitor 162 outputs a notification associated with determining pump 120 to be in the leak condition. For example, state monitor 162 can cause user interface 110 to output a visual indication of the leak condition.

In some embodiments, where NPWT system 100 includes a plurality of pumps 120, pump controller 152 (or a plurality of pump controllers 152 acting in unison) can control operation of the plurality of pumps 120. For example, pump controller 152 can drive a first pump of the plurality of pumps 120 at a first RMS voltage (e.g., a high or maximum RMS voltage), and drive at least one second pump 120 of the plurality of pumps 120 at a second RMS voltage less than the first RMS voltage.

In some embodiments of operation of NPWT system 100, pump controller 152 transmits a first control signal having a first RMS voltage to pump 120 to attempt draw down of the dressing at wound site 106 (e.g., at the start of therapy). The first RMS voltage may be a relatively high value. For example, the first RMS voltage may be 10-11 $V_{rms}$ (it will be appreciated that the RMS voltage values described herein can depend on design characteristics of NPWT system 100 and components thereof). The first control signal may be transmitted for a first period of time that is associated with a threshold time at which it can be expected that a leak is occurring. For example, the first period of time may be approximately 4-5 minutes.

The first RMS voltage may be greater than or equal to a threshold voltage at which driving the at least one piezoelectric pump for at least a second period of time greater than the first period of time causes pump 120 to emit sound at a magnitude greater than a sound threshold. The second period of time may be 8-9 minutes (e.g., 4-5 minutes in addition to the first period of time). As such, if pump 120 is driven at the first RMS voltage for the second period of time, pump 120 will have the unexpected function of emitting an audible sound, which can be used according to the processes described herein to provide an audible alert that NPWT system 100 is not functioning as desired (e.g., is subject to a leak condition). As such, NPWT system 100 may not require the use of separate, dedicated audio output components which would otherwise increase the cost, weight, heat generation, and/or electronic complexity of NPWT system 100.

State monitor 162 can monitor the state of pump 120 to determine whether pump 120 is operating in a leak condition. State monitor 162 can poll monitors 154, 156, 158, 170 to make this determination, such as by receiving an indication from timer 160 that the first period of time has expired and determining whether pump 120 is operating in the leak condition responsive to the first period of time expiration.

If state monitor 162 determines that pump 120 is not operating in the leak condition, then control unit 114 can cause pump 120 to operate in a nominal mode, such as a mode in which pump 120 can run silently indefinitely. For example, by determining that pump 120 is not operating in the leak condition, it can be expected that draw down has been achieved successfully. As such, pump controller 152 can transmit a second control signal having a second RMS voltage to pump 120. The second RMS voltage is less than the first RMS voltage (e.g., second RMS voltage is less than the threshold voltage). The second RMS voltage can be 8-9 $V_{rms}$.

If state monitor 162 determines that pump 120 is operating in the leak condition, state monitor 162 can cause pump controller 152 to transmit a third control signal having a third RMS voltage to pump 120. The third RMS voltage is greater than the second RMS voltage, such as by being greater than or equal to the threshold voltage. In some embodiments, the third RMS voltage is equal to the first RMS voltage. As such, unless pump controller 152 modifies operation of pump 120 by reducing the RMS voltage used to drive pump 120, pump 120 can be expected to emit an audible sound over time, such as after the second period of time has elapsed (if pump 120 has been continually driven at a voltage greater than or equal to the threshold voltage). By modulating the RMS voltage used to drive pump 120 based on whether a leak condition exists, in a manner consistent with the properties of pump 120, control unit 114 can use the unexpected function of the audible noise generated by pump 120 as an audible alert as to a leak condition.

In some embodiments, NPWT system 100 outputs a visual indication of the leak condition, such as by using user interface 110. For example, responsive to determining that the first period of time has expired and that pump 120 is operating in the leak condition, state monitor 162 can cause user interface 110 to output a visual indication that pump 120 is operating in the leak condition. It will be appreciated that state monitor 162 can cause user interface 110 to output a first visual indication at the expiration of the first period of time, and a second visual indication at the expiration of the second period of time.

In some embodiments, NPWT system 100 can continue to reduce the RMS voltage used to drive pump 120 over time if a leak condition does not arise. For example, subsequent to transmitting the second control signal, state monitor 162 can periodically determine whether pump 120 is operating in the leak condition and, in response to determining that pump 120 is not operating in the leak condition, reduce the RMS voltage of the control signal used to drive pump 120, such as to reduce from the 8-9 $V_{rms}$ value of the second RMS voltage to a lower value. Similarly, if state monitor 162 later determines that a leak condition does exist, pump controller 152 can transmit a control signal having an RMS voltage greater than the threshold voltage (which may be reduced again once it is determined that the leak condition no longer exists).

In some embodiments, such as when the leak condition persists to the point where pump 120 is driven above the threshold voltage long enough to generate the audible noise, state monitor 162 can monitor for an indication of a user modification to the wound dressing. In response to receiving the indication, state monitor 162 can cause pump controller 152 to transmit a control signal having an RMS voltage less than the second RMS voltage (e.g., 7 $V_{rms}$).

Control Processes

Figure 4:
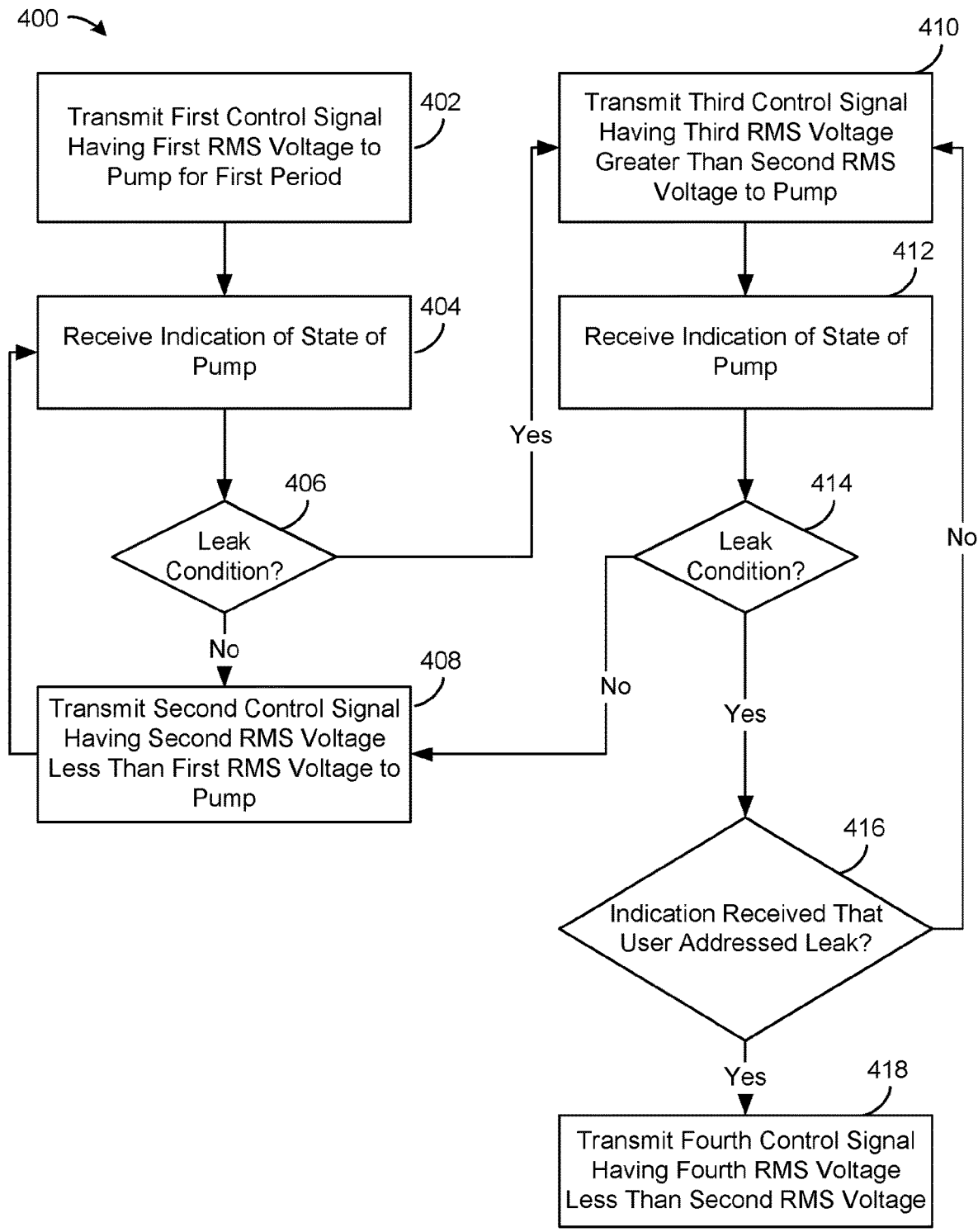
FIG. 4 is a flowchart of a process for operating the NPWT device of FIG. 1, according to an exemplary embodiment.

Referring now to FIG. 4, a flowchart of a process 400 for operating a negative pressure wound therapy (NPWT) device is shown, according to an exemplary embodiment. Process 400 can be performed by one or more components of NPWT system 100, as described with reference to FIGS. 1-3. For example, process 400 can be performed by therapy device 102 using control unit 114 to operate pump 120.

Process 400 is shown to include transmitting a first control signal to at least one piezoelectric pump (step 402). The first control signal can have a first RMS voltage and be transmitted for a first period of time. The first RMS voltage can be greater than or equal to a threshold voltage at which driving the at least one piezoelectric pump for at least a second period of time, which is greater than the first period of time, causes the at least one piezoelectric pump to emit sound at a magnitude greater than a sound threshold. The sound threshold may be associated with silent operation of the at least one piezoelectric pump. For example, the sound threshold can be less than or equal to 30 dB(A). The sound threshold can be zero dB(A).

Process 400 is shown to include receiving an indication of a state of the at least one piezoelectric pump (step 404). The indication can be received from a state detector including at least one of a pressure sensor or a flow rate sensor. The pressure sensor can detect a pressure of at least one of the at least one piezoelectric pump or the wound site. The flow rate sensor can detect a flow rate through the at least one piezoelectric pump, such as by being coupled to the at least one piezoelectric pump or coupled to a point on a flow path from the wound site to the at least one piezoelectric pump.

Process 400 is shown to include determining, based on the indication of the state, whether the at least one piezoelectric pump is operating in a leak condition (step 406). The leak condition may be indicative of the at least one piezoelectric pump failing to complete a draw-down of a wound dressing t the wound site. The leak condition may be consistent with the flow rate through the at least one piezoelectric pump being greater than an expected flow rate for a given RMS voltage at which the at least one piezoelectric pump is being driven.

In some embodiments, such as where the state detector includes the pressure sensor, the leak condition can be determined based on comparing the pressure to a target pressure threshold, and determining the pressure to be less than the target pressure threshold. In some embodiments, such as where the state detector includes the flow rate sensor, the leak condition can be determined based on comparing the flow rate to a flow rate threshold, and determining the flow rate to exceed the flow rate threshold.

Process 400 is shown to include, responsive to determining the at least one piezoelectric pump to not be operating in the leak condition, transmitting a second control signal to the at least one piezoelectric pump (step 408). The second control signal can have a second RMS voltage less than the first RMS voltage. For example, the second RMS voltage can be less than the threshold voltage.

In some embodiments, subsequent to transmitting the second control signal, the indication of state of the at least one piezoelectric pump can be monitored, such as by periodically polling the state detector. In some embodiments, if the at least one piezoelectric pump continues to not operate in the leak condition subsequent to transmission of the second control signal, the RMS voltage used to drive the at least one piezoelectric pump can be decreased.

Process 400 is shown to include, responsive to determining the at least one piezoelectric pump to be operating in the leak condition, transmitting a third control signal having a third RMS voltage greater than the second RMS voltage to the at least one piezoelectric pump (step 410). The third RMS voltage can be greater than or equal to the threshold voltage. For example, the third RMS voltage can be equal to the first RMS voltage. As such, if it is determined that the at least one piezoelectric pump is operating in a leak condition, the at least one piezoelectric can be driven at a voltage sufficient to cause the at least one piezoelectric pump to emit an audible sound, which can provide an alert as to the leak condition.

Process 400 is shown to include receiving an indication of a state of the at least one piezoelectric pump subsequent to transmitting the third control signal (step 412), and determining whether the at least one piezoelectric pump is operating in the leak condition. If the at least one piezoelectric pump is determined to not be operating in the leak condition, then the second control signal may be transmitted to the at least one piezoelectric pump.

If the at least one piezoelectric pump is determined to be operating in the leak condition (subsequent to transmitting the third control signal), then an indication may be monitored for which would indicate that a user addressed the leak (step 416). For example, the indication may be received from a position sensor. The indication may also be detected by calculating a rate of change of a state variable, such as pressure or flow rate, and detecting the indication based on the rate of change exceeding a rate of change threshold, which would indicate a significant change in operation of the NPWT system which could be consistent with user adjustment.

If it is determined than an indication is received that indicates that the user addressed the leak, then a fourth control signal having a fourth RMS voltage less than the second RMS voltage can be transmitted (step 418). Otherwise, the third control signal may be continued to be transmitted to the at least one piezoelectric pump.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A negative pressure wound therapy device, comprising:
   at least one piezoelectric pump configured to apply a vacuum to a wound site;
   a state detector configured to detect a state of the at least one piezoelectric pump; and
   a control circuit configured to:
   transmit a first control signal to the at least one piezoelectric pump to drive the at least one piezoelectric pump for a first period of time, the first control signal having a first root mean square (RMS) voltage, the first RMS voltage greater than or equal to a threshold voltage at which driving the at least one piezoelectric pump for at least a second period of time greater than the first period of time causes the at least one piezoelectric pump to emit sound at a magnitude greater than a sound threshold;
   receive a first indication of the state from the state detector;
   determine, based on the first indication of the state, if the at least one piezoelectric pump is in a leak condition;
   transmit, responsive to the at least one piezoelectric pump not being in the leak condition, a second control signal to the at least one piezoelectric pump to drive the at least one piezoelectric pump, the second control signal having a second RMS voltage less than the first RMS voltage; and
   transmit, responsive to the at least one piezoelectric pump being in the leak condition, a third control signal to the at least one piezoelectric pump to drive the at least one piezoelectric pump, the third control signal having a third RMS voltage greater than the second RMS voltage.

2. The negative pressure wound therapy device of claim 1, wherein the control circuit is configured to execute the determination of whether the at least one piezoelectric pump is in the leak condition responsive to expiration of the first period of time.

3. The negative pressure wound therapy device of claim 1, further comprising a display coupled to the control circuit, wherein the control circuit is configured to cause the display to output a visual indication of the leak condition responsive to determining that the at least one piezoelectric pump is in the leak condition and subsequent to the first period of time.

4. The negative pressure wound therapy device of claim 1, wherein the control circuit is further configured to:
   receive, subsequent to transmitting the second control signal, a second indication of the state from the state detector;
   determine, based on the second indication of the state, if the at least one piezoelectric pump is in the leak condition;

transmit, responsive to the at least one piezoelectric pump not being in the leak condition, a subsequent control signal to the at least one piezoelectric pump to drive the at least one piezoelectric pump, the subsequent control signal having an RMS voltage less than the second RMS voltage; and transmit, responsive to the at least one piezoelectric pump being in the leak condition, the third control signal to the at least one piezoelectric pump to drive the at least one piezoelectric pump, the third control signal having the third RMS voltage greater than the second RMS voltage.

5. The negative pressure wound therapy device of claim 1, further comprising a housing at least partially surrounding the at least one piezoelectric pump, the housing configured to increase a loudness outside of the housing of the sound emitted by the at least one piezoelectric pump.

6. The negative pressure wound therapy device of claim 5, wherein the housing is shaped to facilitate gas venting from the at least one piezoelectric pump.

7. The negative pressure wound therapy device of claim 1, wherein the first RMS voltage is an average RMS voltage, and the control circuit is configured to modulate the first RMS voltage by at least one of modulating a duty cycle or a magnitude of the first control signal.

8. The negative pressure wound therapy device of claim 1, wherein the control circuit is further configured to receive an indication of a user modification of a dressing adjacent to the wound site, and transmit a fourth control signal having a fourth RMS voltage less than the second RMS voltage to the at least one piezoelectric pump responsive to receiving the indication.

9. The negative pressure wound therapy device of claim 1, wherein the state detector includes at least one of:
(i) a flow rate sensor coupled to the at least one piezoelectric pump, the flow rate sensor configured to detect a flow rate through the at least one piezoelectric pump, wherein the control circuit is configured to compare the detected flow rate to a flow rate threshold, and determine the at least one piezoelectric pump to be operating in the leak condition responsive to the flow rate exceeding the flow rate threshold; or
(ii) a pressure sensor configured to detect a pressure of at least one of the at least one piezoelectric pump or the wound site, wherein the control circuit is configured to compare the pressure detected by the pressure sensor to a target pressure threshold, and determine the at least one piezoelectric pump to be operating in the leak condition responsive to the pressure being less than the target pressure threshold.

10. The negative pressure wound therapy device of claim 1, wherein the sound threshold is zero dB(A).

11. A method, comprising:
transmitting a first control signal to at least one piezoelectric pump to drive the at least one piezoelectric pump for a first period of time, the at least one piezoelectric pump configured to apply a vacuum to a wound site, the first control signal having a first root mean square (RMS) voltage, the first RMS voltage greater than or equal to a threshold voltage at which driving the at least one piezoelectric pump for at least a second period of time greater than the first period of time causes the at least one piezoelectric pump to emit sound at a magnitude greater than a sound threshold;
receiving, from a state detector configured to detect a state of the at least one piezoelectric pump, a first indication of the state;
determining, based on the first indication of the state, if the at least one piezoelectric pump is in a leak condition;
transmitting, responsive to the at least one piezoelectric pump not being in the leak condition, a second control signal to the at least one piezoelectric pump to drive the at least one piezoelectric pump for a third period of time, the second control signal having a second RMS voltage less than the first RMS voltage; and
transmitting, responsive to the at least one piezoelectric pump being in the leak condition, a third control signal to the at least one piezoelectric pump to drive the at least one piezoelectric pump, the third control signal having a third RMS voltage greater than the second RMS voltage.

12. The method of claim 11, wherein determining whether the at least one piezoelectric pump is in the leak condition includes determining whether the at least one piezoelectric pump is in the leak condition responsive to expiration of the first period of time.

13. The method of claim 11, further comprising causing a display to output a visual indication of the leak condition responsive determining that the at least one piezoelectric pump is in the leak condition and subsequent to the first period of time.

14. The method of claim 11, further comprising:
receiving, responsive to the third period of time expiring, a second indication of the state from the state detector;
determining, based on the second indication of the state, if the at least one piezoelectric pump is in the leak condition;
transmitting, responsive to the at least one piezoelectric pump not being in the leak condition, a subsequent control signal to the at least one piezoelectric pump to drive the at least one piezoelectric pump, the subsequent control signal having an RMS voltage less than the second RMS voltage; and
transmitting, responsive to the at least one piezoelectric pump being in the leak condition, the third control signal to the at least one piezoelectric pump to drive the at least one piezoelectric pump, the third control signal having the third RMS voltage greater than the second RMS voltage.

15. The method of claim 11, further comprising providing a housing to at least partially surround the at least one piezoelectric pump, the housing configured to increase a loudness outside of the housing of the sound emitted by the at least one piezoelectric pump.

16. The method of claim 15, wherein the housing is shaped to facilitate gas venting from the at least one piezoelectric pump.

17. The method of claim 11, wherein the first RMS voltage is an average RMS voltage, and transmitting the first control signal includes generating the first control signal by modulating at least one of a duty cycle or a magnitude of the first control signal.

18. The method of claim 11, further comprising receiving an indication of a user modification of a dressing adjacent to the wound site, and transmitting a fourth control signal having a fourth RMS voltage less than the second RMS voltage to the at least one piezoelectric pump responsive to receiving the indication.

19. The method of claim 11, wherein the state detector includes at least one of:
(i) a flow rate coupled to the at least one piezoelectric pump, the leak detector configured to detect a flow rate through the at least one piezoelectric pump, wherein determining the at least one piezoelectric pump to be operating in the leak condition includes determining the flow rate to exceed a flow rate threshold; or (ii) a pressure sensor configured to detect a pressure of at least one of the at least one piezoelectric pump or the wound site, wherein determining the at least one piezoelectric pump to be operating in the leak condition includes determining the pressure to be less than a target pressure threshold.

20. The method of claim 11, wherein the sound threshold is zero dB(A).

* * * * *